(12) United States Patent
Zhang

(10) Patent No.: US 10,392,342 B1
(45) Date of Patent: Aug. 27, 2019

(54) USE OF AGGREGATION-INDUCED EMISSION COMPOUNDS IN DISPERSION DETECTING OF NANOPARTICLES

(71) Applicant: BOE TECHNOLOGY GROUP CO., LTD., Beijing (CN)

(72) Inventor: Zhenqi Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 16/150,115

(22) Filed: Oct. 2, 2018

(30) Foreign Application Priority Data

Mar. 29, 2018 (CN) .......................... 2018 1 0273043

(51) Int. Cl.
| | | |
|---|---|---|
| *C07C 229/24* | (2006.01) |
| *C07C 255/42* | (2006.01) |
| *C09K 11/06* | (2006.01) |
| *G01N 15/06* | (2006.01) |
| *G01N 15/00* | (2006.01) |

(52) U.S. Cl.
CPC .......... *C07C 229/24* (2013.01); *C07C 255/42* (2013.01); *C09K 11/06* (2013.01); *G01N 15/06* (2013.01); *C09K 2211/1007* (2013.01); *C09K 2211/1014* (2013.01); *G01N 2015/0038* (2013.01); *G01N 2015/0053* (2013.01); *G01N 2015/0681* (2013.01); *G01N 2015/0693* (2013.01)

(58) Field of Classification Search
CPC ..... C07C 229/24; C07C 255/42; C09K 11/06; C09K 2211/1007; C09K 2211/1014; G01N 15/06; G01N 2015/0038; G01N 2015/0053; G01N 2015/0681; G01N 2015/0693
See application file for complete search history.

(56) References Cited

U.S. PATENT DOCUMENTS

2015/0148262 A1* 5/2015 Trau .................. G01N 33/5432
506/20

* cited by examiner

*Primary Examiner* — Mark R Gaworecki
(74) *Attorney, Agent, or Firm* — Foley & Lardner LLP

(57) ABSTRACT

Provided is a use of an aggregation-induced emission compound in dispersion detecting of nanoparticles. The dispersion detecting of nanoparticles includes modifying the aggregation-induced emission compound on the surfaces of the nanoparticles to obtain a modified nanoparticles solution. The dispersion detecting of nanoparticles includes exciting the modified nanoparticles solution and determining the dispersion of the nanoparticles by the luminescence state of the solution.

10 Claims, 2 Drawing Sheets

USE OF AGGREGATION-INDUCED EMISSION COMPOUNDS IN DISPERSION DETECTING OF NANOPARTICLES

CROSS-REFERENCE TO RELATED APPLICATIONS

This application claims priority to Chinese Patent Application No. 201810273043.5, filed on Mar. 29, 2018, the entire contents of which are incorporated herein be reference.

TECHNICAL FIELD

This disclosure relates to the field of nanomaterials, and particularly to the use of aggregation-induced emission compounds in dispersion detecting of nanoparticles.

BACKGROUND

Nanomaterials usually have special mechanical, optical, magnetic, electrical, catalytic and other characteristics, so they are significantly valuable for applications. For example, ZnO and ZnMgO nanoparticles can be used in charge transport layer of QLED; $Fe_3O_4$ magnetic nanoparticles can be used for biological separation, magnetic hyperthermia, targeted drug delivery and magnetic resonance imaging; nano-Ag can be used for antibiosis, catalysis, conductive ink, etc. Additionally, if prepared as nanoparticles, the catalytic effect of metallic catalysts such as Fe, Co, Ni, Pd and Pt can be considerably improved. Specifically, Ni powder in sized 30 nm can make the rate of organic chemical hydrogenation or dehydrogenation reaction increased by 15 times. Further, the sintering temperature of $Si_3N_4$ is conventionally above 2000° C., while the sintering temperature of nano-$Si_3N_4$ can decrease to 1500-1600° C., and the sintered products can obtain a hardness and strength higher than ordinary ceramics by 4 to 5 times.

SUMMARY

In view of the problems in the prior art, the present disclosure provides the technical solutions as followed.

The present disclosure provides the use of an aggregation-induced emission compound in dispersion detecting of nanoparticles.

In one or more arrangements, the aggregation-induced emission compound is selected from one or more of the following structures:

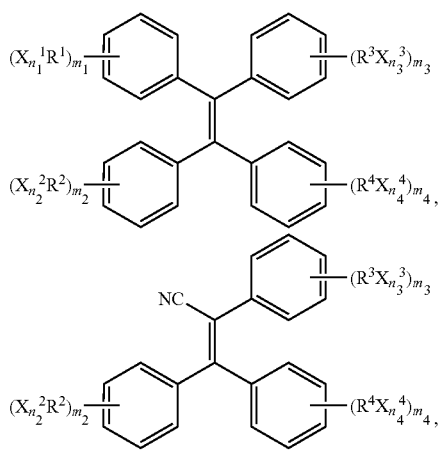

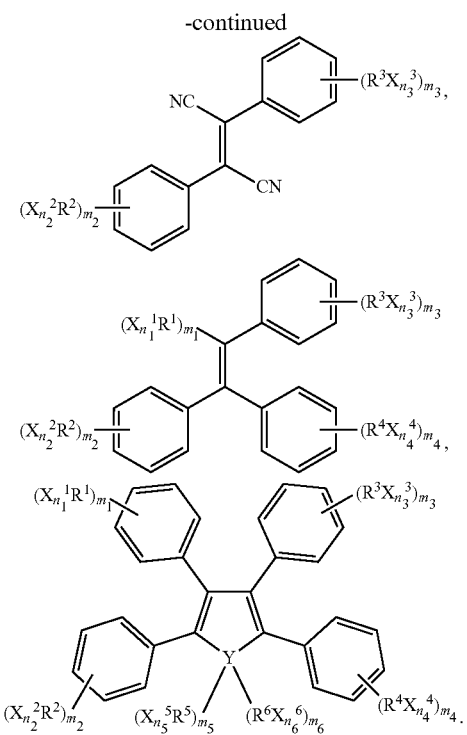

For example, $R^1$, $R^2$, $R^3$, $R^4$, $R^5$ and $R^6$ are each independently selected from the group consisting of a chemical bond, hydrogen, a saturated alkyl group, an unsaturated alkyl group, a heteroalkyl group, a cycloalkyl group, a heterocycloalkyl group, an aryl group, a heteroaryl group and an alkoxy group.

For example, $X^1$, $X^2$, $X^3$, $X^4$, $X^5$ and $X^6$ are each independently selected from one of an amino group, a hydroxyl group, a thiol group, a carboxyl group, a sulfonic acid group, a phosphine and a phosphine oxide.

For example, $m_1$, $m_2$, $m_3$, $m_4$, $m_5$ and $m_6$ are each independently 1, 2 or 3;

$n_1$, $n_2$, $n_3$, $n_4$, $n_5$ and $n_6$ are each independently 0, 1, 2 or 3, and are not 0 at the same time.

For example, Y is selected from one of C, O, N, S and Si.

In one or more arrangements, the nanoparticles are selected from one or more of the group consisting of metal nanoparticles, inorganic nanoparticles, polymeric nanospheres, and organic-inorganic hybrid nanoparticles.

In one or more arrangements, the metal nanoparticles are selected from one or more of Fe, Co, Ni, Pd, Pt, Ag and Au.

In one or more arrangements, the inorganic nanoparticles are selected from one or more of the group consisting of $SiO_2$, $TiO_2$, ZnO, $Si_3N_4$, CdSe and PbS.

In one or more arrangements, the polymeric nanospheres are selected from one or more of polystyrene, polylactic acid, chitosan and protein microspheres.

In one or more arrangements, the dispersion detecting of nanoparticles includes modifying the aggregation-induced emission compound on the surfaces of the nanoparticles to obtain a modified nanoparticles solution. The dispersion detecting of nanoparticles includes exciting the modified nanoparticles solution and determining the dispersion of the nanoparticles by the luminescence state of the solution.

In one or more arrangements, the mass ratio of the nanoparticles to the aggregation-induced emission compound is in a range from 10:1 to 1:100.

In one or more arrangements, the mass ratio of the nanoparticles to the aggregation-induced emission compound is preferably in a range from 3:1 to 1:3.

In one or more arrangements, the excitation is ultraviolet light excitation, infrared light excitation, far infrared light excitation, visible light excitation or chemical energy excitation.

In one or more arrangements, the modified nanoparticles solution after excited has a luminescence which is fluorescence, phosphorescence or delayed phosphorescence.

In one or more arrangements, if the modified nanoparticles solution after excited has no luminescence or an extremely weak luminescence, it is determined that the nanoparticles are in a dispersed state; if the modified nanoparticles solution after excited has a strong luminescence or a significantly enhanced luminescence, it is determined that the nanoparticles are in an aggregated state or a coagulated state.

DETAILED DESCRIPTION

Figure 1:
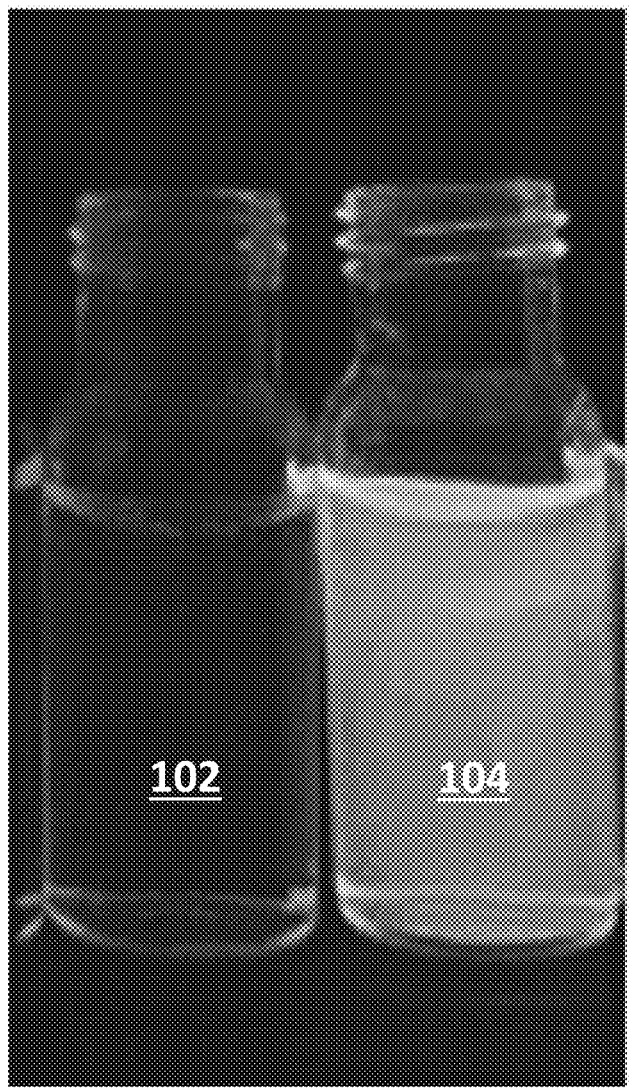
FIG. 1 is a graph comparing the luminescence of two excited solutions of the nanoparticles according to Example 1.

The technical solution of this disclosure will be described in more detail with reference to the following examples. The scope of this disclosure is not limited to the examples, which are given only for illustrative purposes and are not intended to limit the disclosure in any way.

The special characteristics of nanomaterials are contributed to their nanoscale. Therefore, if nanoparticles coagulate, their performance will be seriously affected. Due to the small size and large specific surface area, nanoparticles tend to coagulate under the effect of charge or collision. Very severe coagulation can lead to precipitation, which can be visual detected directly. While most of the coagulations can not be observed by eyes, and need to be detected via instruments such as scanning electron microscopy (SEM), transmission electron microscopy (TEM) and particle analyzer. Accordingly, it will be much harder for the users to determine the state of coagulation.

Luminescence of conventional fluorescent compounds often becomes quenched when they are in the aggregated state. While the aggregation-induced emission (AIE) compounds have a weak luminescence when in a single molecule state in the solution, however, they will have a strong luminescence when in the aggregated state.

Depending on the molecular structure, the aggregation-induced emission compounds in the aggregate state can be excited by ultraviolet light, visible light, infrared light, far-infrared light, chemical energy, etc., and emit fluorescence, phosphorescence or delayed fluorescence in the visible band to the human eyes.

For example, the aggregation-induced emission compounds are selected from one or more of the following structures:

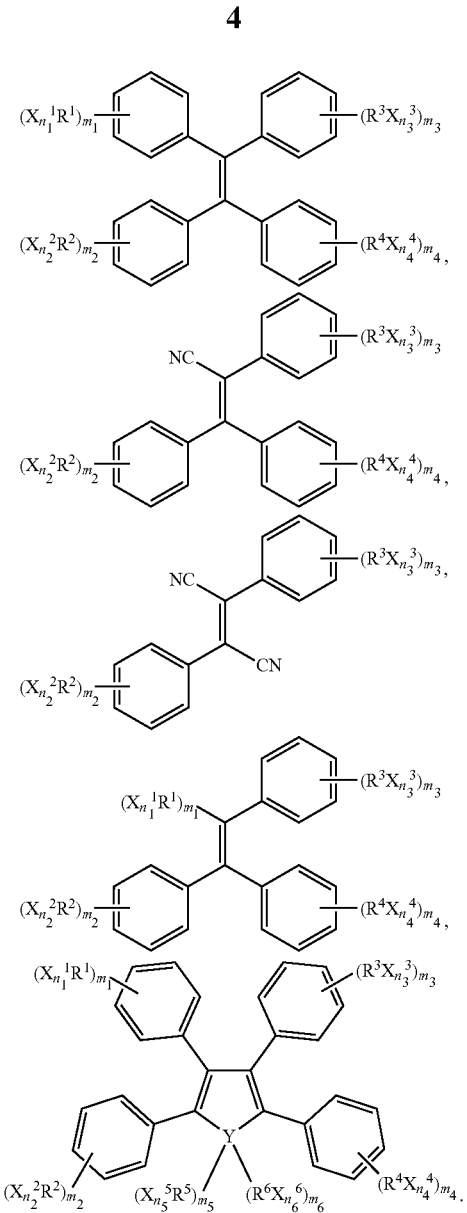

$R^1$, $R^2$, $R^3$, $R^4$, $R^5$ and $R^6$ are each independently selected from the group consisting of a chemical bond, hydrogen, a saturated alkyl group, an unsaturated alkyl group, a heteroalkyl group, a cycloalkyl group, a heterocycloalkyl group, an aryl group, a heteroaryl group and an alkoxy group.

$X^1$, $X^2$, $X^3$, $X^4$, $X^5$ and $X^6$ are each independently selected from one of an amino group, a hydroxyl group, a thiol group, a carboxyl group, a sulfonic acid group, a phosphine and a phosphine oxide.

$m_1$, $m_2$, $m_3$, $m_4$, $m_5$ and $m_6$ are each independently 1, 2 or 3.

$n_1$, $n_2$, $n_3$, $n_4$, $n_5$ and $n_6$ are each independently 0, 1, 2 or 3, and are not 0 at the same time.

Y is selected from one of C, O, N, S and Si.

The term "alkyl" as used herein, refers to a branched or unbranched "hydrocarbyl" chain containing a defined amount of carbon (C) atoms. For example, a short chain of a $C_1$-$C_6$ straight or branched hydrocarbon group contains 1 to 6 carbon atoms. These include, but are not limited to, methyl, ethyl, propyl, isopropyl, butyl, isobutyl, tert-butyl, n-pentyl, n-hexyl, and the like. In particular arrangements, the "hydrocarbyl" chain can be unsubstituted or have one or more substituents.

The term "cycloalkyl" refers to an organic cyclic substituent containing the defined amount of carbon atoms. For example, a $C_3$-$C_8$ cycloalkyl group contains 3 to 8 carbon atoms which can form a three-membered, four-membered, five-membered, six-membered, seven-membered or eight-membered ring, including, but not limited to, cyclopropyl, cyclobutyl, cyclopentyl, cyclohexyl, cycloheptyl or cyclooctyl. In a particular arrangement, "cycloalkyl" can be unsubstituted or have one to more substituents.

The term "aryl" refers to an aromatic carbocyclic group which can be a monocyclic ring (eg. a phenyl ring), a polycyclic ring (eg. a biphenyl group), or a plurality of fused rings having at least one aromatic ring (eg. naphthyl, 1,2,3,4-tetrahydronaphthyl, anthracenyl and phenanthryl). The aryl group can be unsubstituted or have one or more substituents.

The term "heteroaryl" refers to a heterocyclic group having at least one aromatic ring. It can be a saturated, unsaturated and/or aromatic carbocyclic group having a single ring, multiple rings or multiple fused rings and having at least one hetero atom such as N, O, S or P. The heteroaryl group can also include a heteroalkyl group or a heterocycloalkyl group. In one arrangement, "heteroaryl" can be unsubstituted or have one or more substituents.

The term "alkoxy" refers to an alkyl group. The carbon atom is bonded to the oxygen atom by a single bond. The alkoxy group has a large range of variety. The simplest one is methoxy ($CH_3O$—), and can also be a structure formed by a plurality of ethoxy groups bonded, for example, —$(OCH_2CH_2)_p$—. p is an integer in a range from 2 to 8. Generally, it can be any alkyl group in which one or more carbon atoms are bonded to oxygen atoms by single bonds.

With respect to the structure, the above-mentioned aggregation-induced emission compound mainly includes a coordination moiety and an active moiety. In above formulas, $X^1$, $X^2$, $X^3$, $X^4$, $X^5$ and $X^6$ act as the coordination moiety to combine with the nanoparticles, so that the aggregation-induced emission compound and the nanoparticles can be bonded by a chemical bond or a weak intermolecular force such as Van der Waals force or hydrogen bond. While the main structures in above formulas act as the active moiety, and the typical functional group includes tetraphenylethylene, triphenylethylene, cyano triphenylethylene, tetraphenylsilole and their derivatives.

Certain structures of the active moiety are as follows:

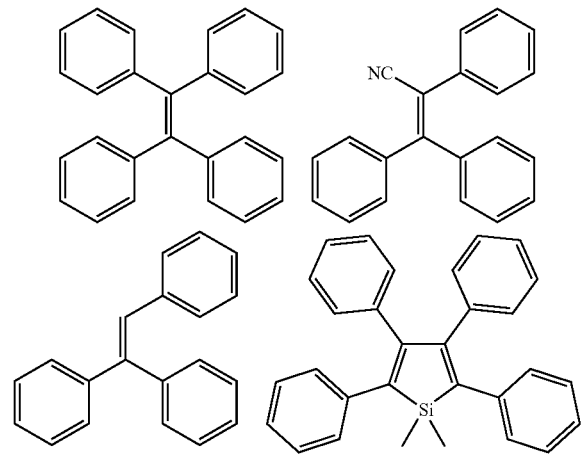

$m_1$, $m_2$, $m_3$, $m_4$, $m_5$ and $m_6$ are each independently 1, 2 or 3. It means that one, two or three RX groups can be respectively bonded to the main structure at each position, and when R is a chemical bond, X groups (i.e., $X^1$, $X^2$, $X^3$, $X^4$, $X^5$ and $X^6$) are directly bonded to the main structure.

$n_1$, $n_2$, $n_3$, $n_4$, $n_5$ and $n_6$ are each independently 0, 1, 2 or 3 and can not be 0 at the same time. It means that, in the above structures, $R^1$, $R^2$, $R^3$, $R^4$, $R^5$ and $R^6$ each can be bonded to one, two or three X groups, or some of them can not bonded to X group (for example, when R is hydrogen), but at least one X group is directly or indirectly bonded to the main structure.

At least one of $R^1X^1$, $R^2X^2$, $R^3X^3$, $R^4X^4$, $R^5X^5$ and $R^6X^6$ acts as a coordinating moiety to combine with the nanoparticles, and the remaining RX can combine with selected group as desired. For example, when one or more of $R^1$, $R^2$, $R^3$, $R^4$, $R^5$ and $R^6$ is —$(OCH_2CH_2)_p$—, $X^1$, $X^2$, $X^3$, $X^4$, $X^5$ and $X^6$ bonded thereto can be a hydroxyl group. The structure formed can adjust the solubility of the compound in the solution, which makes the compound easy to react and combine with the nanoparticles in the solution. Of course, according to this disclosure, the combination of RX groups which can be used to adjust the solubility is not limited thereto, and can also be an aromatic thiol (for example, —$C_6H_4SH$, —$C_6H_4CH_2CH_2SH$), an aliphatic thiol (for example, —$CH_2CH_2CH_2CH_2SH$), an amino compound (—$NHCH_2CH_2NH_2$), or the like.

Particularly, the combination of the aggregation-induced emission compound and the nanoparticles includes mixing the solution containing the nanoparticles with the aggregation-induced emission compound. After the reaction therebetween for a while, the aggregation-induced emission compound can be modified on the surfaces of the nanoparticles.

The combination of the aggregation-induced emission compound and the nanoparticles can be promoted by heating, stirring, ultrasonication, microwave, and the like. The unstable nanoparticle can be protected by inert gas such as nitrogen or argon. The combination process can be carried out simultaneously during the synthesis of the nanoparticles or after the synthesis of the nanoparticles.

According to this disclosure, the nanoparticles are selected from one or more of metal nanoparticles, inorganic nanoparticles, polymer nanospheres, and organic-inorganic hybrid nanoparticles. The metal nanoparticles are selected from one or more of Fe, Co, Ni, Pd, Pt, Ag and Au, the inorganic nanoparticles are selected from one or more of $SiO_2$, $TiO_2$, ZnO, $Si_3N_4$, CdSe and PbS, and the polymer nanospheres are selected from one or more of polystyrene, polylactic acid, chitosan and protein microspheres.

The dispersion detecting of the nanoparticles, which usually is carried out in a solution, includes producing a modified nanoparticles solution by using the above nanoparticle modification method. The dispersion detecting of nanoparticles includes exciting the modified nanoparticle solution by a suitable way. The dispersion detecting of nanoparticles includes determining the dispersion of the nanoparticles by the luminescence of the modified nanoparticle solution after the excitation.

Specifically, it can be determined whether the aggregation-induced emission compound exists in a dispersion state or a coagulation state according to its luminescence, and since the aggregation-induced emission compound is combined with the nanoparticles, it also can be determined whether the nanoparticles exist in a dispersion state or a coagulation state.

The modified nanoparticles solution usually can be excited by ultraviolet light, infrared light, far infrared light or visible light. A suitable excitation source can be selected depending on the molecular structure of the aggregation-induced emission compound, to make the compound emit fluorescence, phosphorescence or delayed fluorescence. Additionally, the modified nanoparticles solution also can be excited by chemical energy ($H_2O_2$) in the presence of a photosensitizer, to effectively generate singlet oxygen and near-infrared spontaneous fluorescence.

The dispersion of the nanoparticles can be determined by a naked eye. When the modified nanoparticles solution has no or an extremely weak luminescence after excited, it means that the aggregation-induced emission compound is well dispersed, and the nanoparticles are also in a dispersed state. When the modified nanoparticles solution has a strong or a significantly enhanced luminescence after excited, it means that the aggregation-induced emission compound is aggregated, and the nanoparticles are also in an aggregated or coagulated state. Unless otherwise defined, the terms used in this disclosure are intended to be understood by those of ordinary skilled in the art.

Hereinafter, the present disclosure will be further described in detail by following examples.

Example 1

1.1 the Synthesis of the Aggregation-Induced Emission Compound

The aggregation-induced emission compound was prepared as followed:

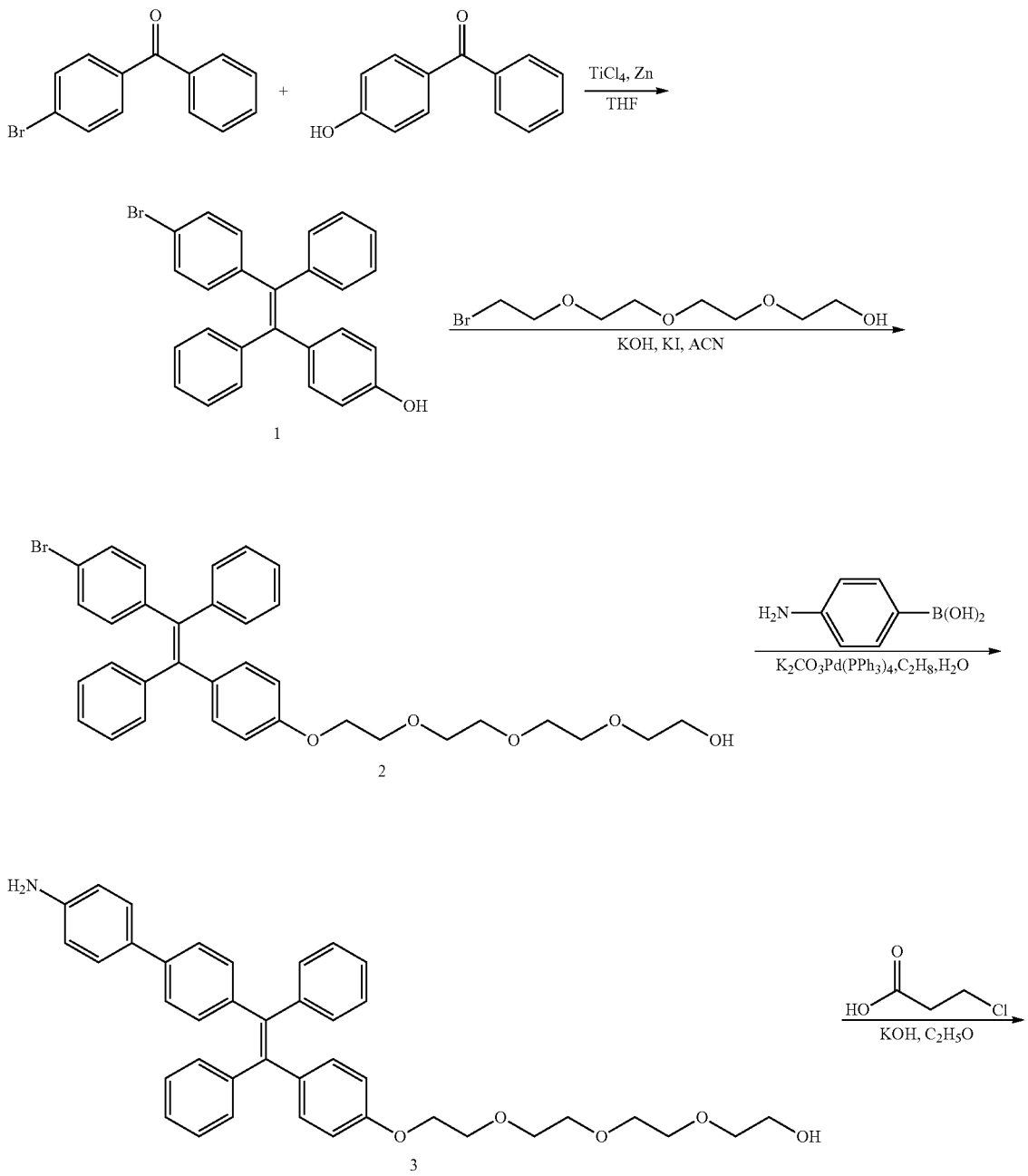

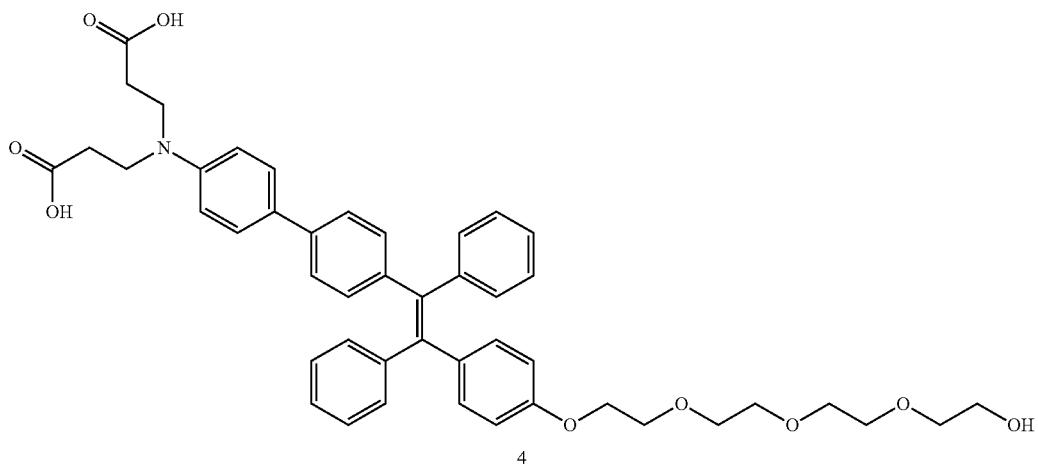

4

Specifically, 4-bromobenzophenone (10 mmol), 4-hydroxybenzophenone (10 mmol) and zinc powder (40 mmol) were added to a 250 ml three-necked flask, and then dry tetrahydrofuran (100 ml) was added.

The system was slowly injected with carbon tetrachloride (20 mmol) under a nitrogen atmosphere and ice-water bath condition and then was slowly heated to room temperature, and subsequently reflux was carried out for 5 hours. After the reaction was completed, the mixture was filtered, and the filtrate was evaporated to dryness. After neutralized with hydrochloric acid, it was extracted with ethyl acetate, and then the organic phase was evaporated to dryness and the product was purified by column chromatography to give Compound 1.

Compound 1 (10 mmol) and potassium hydroxide (20 mmol) were dissolved in acetonitrile (100 ml) and reacted at 60° C. for 2 hours, and then 2-{2-[2-(2-bromoethoxy) ethoxy]ethoxy}ethanol (15 mmol) and potassium iodide (2 mmol) were added thereto and reacted at 60° C. for 10 hours. After the reaction was completed, the mixture was evaporated to dryness and then purified by column chromatography to give compound 2.

P-aminophenylboronic acid (11 mmol), compound 2 (10 mmol), potassium carbonate (30 mmol) and tetratriphenylphosphine (0.5 mmol) were added to a flask, and then 50 ml of water and 50 ml of toluene were added thereto. Reflux was carried out under a nitrogen atmosphere for 12 hours. After the reaction was completed, the reaction mixture was evaporated to dryness and purified by column chromatography to give compound 3.

3-Chloropropionic acid (25 mmol), compound 3 (10 mmol), potassium hydroxide (25 mmol) was dissolved in ethanol (100 ml), and then reflux was carried out for 24 hours. After the reaction was completed, the product was neutralized by adding dilute hydrochloric acid, and then the solvent was evaporated to dryness, followed by column chromatography purification to obtain a aggregation-induced emission ligand compound 4.

1.2 the Synthesis of Nanoparticles

Zinc acetate dihydrate (3 mmol) was dissolved in DMSO (30 ml), tetrabutylammonium hydroxide (5.5 mmol) was dissolved in ethanol (10 ml), and then they were mixed and stirred at room temperature for 24 hours. An appropriate amount of ethyl acetate was added, and a precipitate was deposited. The precipitate was centrifuged to obtain zinc oxide nanoparticles.

1.3 the Modification of the Nanoparticles

Zinc oxide nanoparticles were dissolved in an ethanol solution containing an appropriate amount of the aggregation-induced emission compound (a compound synthesized in 1.1). The mass ratio of the nanoparticles to the aggregation-induced emission compound is in a range from 10:1 to 1:100, preferably from 3:1 to 1:3. The solution was stirred at room temperature for 3 hours. Ethyl acetate was then added to make a precipitate deposited and the mixture was centrifuged to separate the precipitate. The obtained precipitate was dissolved again in ethanol to obtain a modified zinc oxide nanoparticles solution.

1.4 Dispersion Detecting of the Nanoparticles

The modified zinc oxide nanoparticles solution was divided into two parts, which were respectively recorded as nanoparticle solution a and nanoparticle solution b.

The nanoparticle solution a was irradiated with ultraviolet light. After observed by a naked eye, it was found that the solution has no or an extremely weak luminescence, and therefore it can be determined that the nanoparticle solution a was in a dispersed state.

Water was added to the nanoparticle solution b, and then the solution was aged for 48 hours. Subsequently, the solution was irradiated with ultraviolet light and was found to emit strong fluorescence. Therefore, it can be determined that the nanoparticle solution b was in a coagulated state.

The luminescence state of the nanoparticle solution a and the nanoparticle solution b after irradiated by ultraviolet light was shown in FIG. 1. The left one (102) is the nanoparticle solution a and the right one (104) is the nanoparticle solution b.

Then, the nanoparticle solution a and the nanoparticle solution b were subjected to a particle size test and a luminescence intensity test respectively, and the test results were shown in Table 1 and Table 2.

TABLE 1 results of the particle size test

| nanoparticle solution a | | nanoparticle solution b | |
| --- | --- | --- | --- |
| Diameter (nm) | Volume (%) | Diameter (nm) | Volume (%) |
| 3 | 4 | 3 | 1 |
| 4 | 21 | 4 | 2 |
| 5 | 45 | 5 | 3 |
| 6 | 23 | 6 | 3 |
| 7 | 7 | 7 | 2 |
| | | 95-98 | 4 |
| | | 99-102 | 8 |
| | | 102-106 | 5 |
| | | 188-191 | 7 |
| | | 192-195 | 15 |
| | | 196-199 | 24 |
| | | 200-203 | 14 |
| | | 204-207 | 7 |
| | | 208-211 | 5 |

It can be seen from Table 1 that the particle size of the nanoparticle solution a was below 7 nm, which indicated that the solution was obviously in a dispersed state, and the particle size of the nanoparticle solution b was up to 200 nm, which indicated that the solution was obviously in a coagulated state. Therefore, it demonstrated that the results of the dispersion detecting according to the present disclosure was consistent with the results of the particle size test.

TABLE 2 the change of the luminescence intensity and quantum yield

| | nanoparticle solution a | nanoparticle solution b | increase multiple |
| --- | --- | --- | --- |
| luminescence intensity at 450 nm | 20 | 320 | 16 |
| luminescence quantum yield | 0.01 | 0.15 | 150 |

It can be seen from Table 2 that, at 450 nm, the luminescence intensity of the nanoparticle solution b was 16 times higher than that of the nanoparticle solution a, and the luminescence yield was 150 times higher, which indicated that the luminescence of the nanoparticle solution b was much stronger than that of the nanoparticle solution a and can be observed by a naked eye.

Example 2

2.1 the Synthesis of the Aggregation-Induced Emission Compound

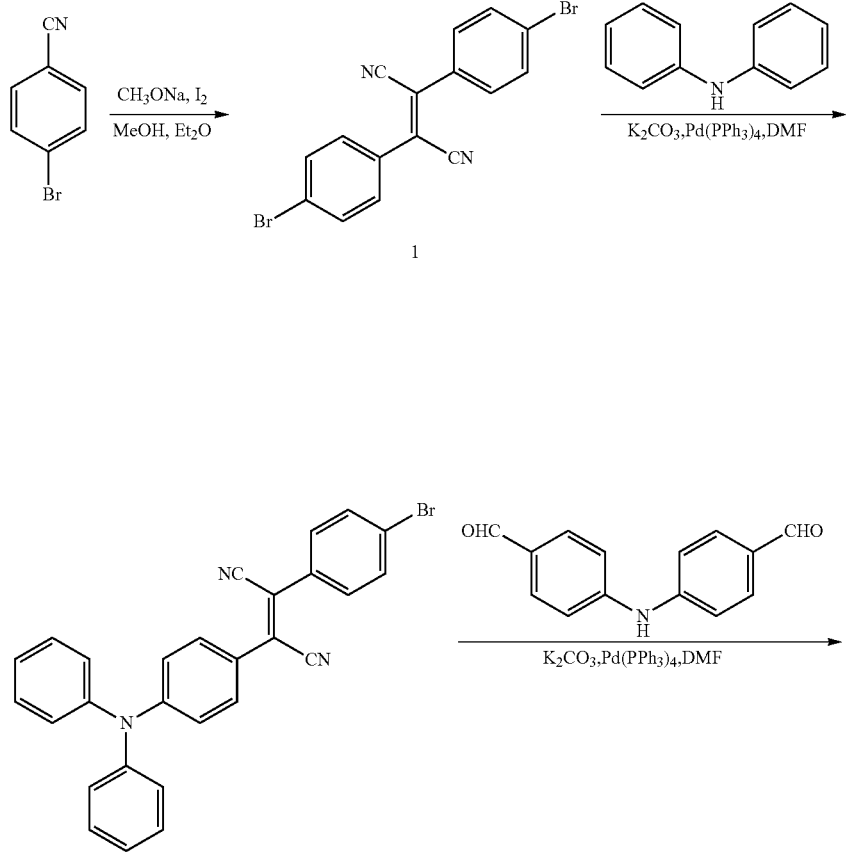

-continued

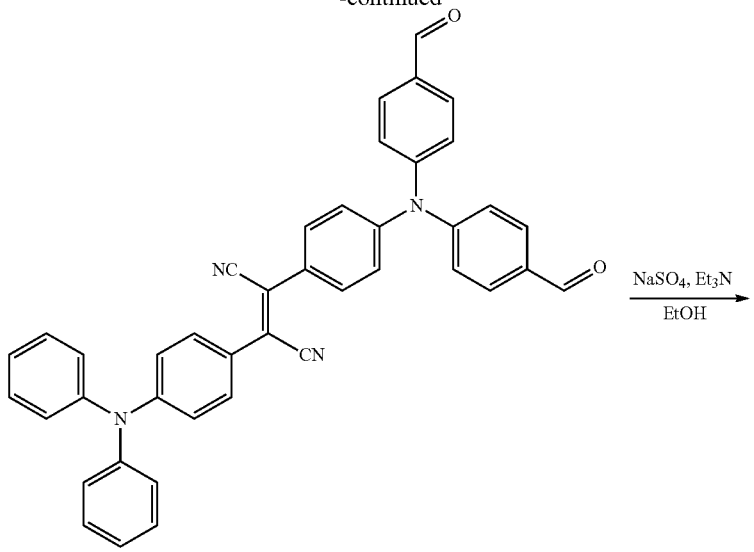

3

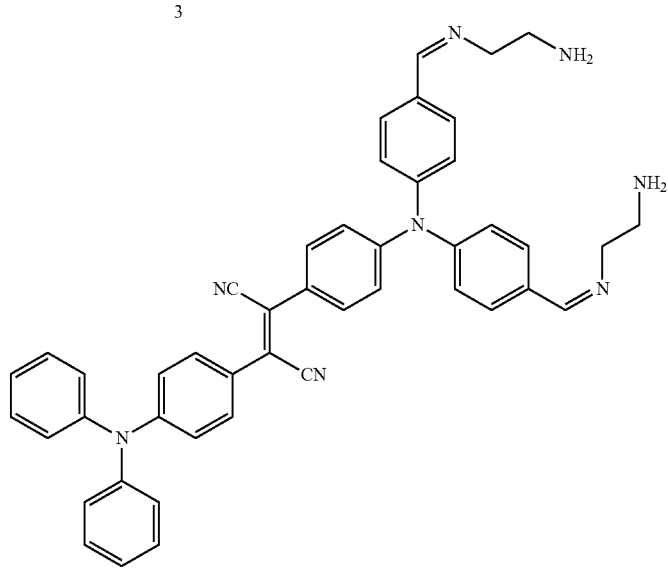

4

P-bromophenylacetonitrile (12.5 mmol) and iodine (12.5 mmol) were dissolved in dry ether (80 ml), and then the system was cooled to −78° C. under a nitrogen atmosphere. Subsequently, sodium methoxide (25 mmol) and methanol (10 ml) were gradually added and stirred for 30 minutes. Following, the system was slowly heated to 0° C. and stirred for 5 hours in an ice-water bath. Then, 5% dilute hydrochloric acid (50 ml) was gradually dropped thereto and the temperature of the system was kept below 10° C. when added.

After the reaction was completed, the mixture was filtered with suction, and the filter cake was washed with a methanol/water (v/v=1/1) mixed solution, dried and purified by column chromatography to give compound 1.

Compound 1 (10 mmol) and diphenylamine (9.5 mmol) were dissolved in N,N-dimethylformamide, and then potassium carbonate (30 mmol) and tetratriphenylphosphine palladium (0.3 mmol) were added thereto. The system was refluxed for 24 hours under a nitrogen atmosphere. After the reaction was completed, the system was poured into water, and then a solid precipitate was deposited. After filtrating, the filter cake was dried and purified by column chromatography to give compound 2.

Compound 2 (10 mmol) and 4,4'-dialdehyde diphenylamine (9.5 mmol) were dissolved in N,N-dimethylformamide, and then potassium carbonate (30 mmol) and tetratriphenylphosphine palladium (0.3 mmol) were added thereto. The system was refluxed for 24 hours under a nitrogen atmosphere. After the reaction was completed, the system was poured into water, and then a solid precipitate was deposited. After filtrating with suction, the filter cake was dried and purified by column chromatography to obtain compound 3.

Compound 3 (10 mmol), ethylenediamine (30 mmol), sodium sulfate (100 mmol) and triethylamine (30 mmol) were added to ethanol. After stirring at room temperature for 5 hours, a solid precipitate was deposited. Filtration was carried out to obtain a solid which was washed with water to remove sodium sulfate. The solid was further subjected to purifying by column chromatography to give the aggregation-induced emission ligand compound 4.

2.2 the Synthesis of the Nanoparticles

Zinc acetate dihydrate (3 mmol) was dissolved in DMSO (30 ml), tetrabutylammonium hydroxide (5.5 mmol) was dissolved in ethanol (10 ml), and they were mixed and stirred at room temperature for 24 hours. An appropriate amount of ethyl acetate was added, and a precipitate was deposited. The precipitate was centrifuged to obtain zinc oxide nanoparticles.

2.3 the Modification of the Nanoparticles

Zinc oxide nanoparticles were dissolved in an chloroform solution containing an appropriate amount of the aggregation-induced emission compound (a compound synthesized in 2.1). The mass ratio of the nanoparticles to the aggregation-induced emission compound is in a range from 10:1 to 1:100, preferably from 3:1 to 1:3. The solution was stirred at room temperature for 1 hour. Ethyl acetate was then added to make a precipitate deposited and the mixture was centrifuged to separate the precipitate. The obtained precipitate was dissolved again in chloroform to obtain a modified zinc oxide nanoparticles solution.

2.4 Dispersion Detecting of the Nanoparticles

The modified zinc oxide nanoparticles solution was divided into two parts, which were respectively recorded as nanoparticle solution c and nanoparticle solution d.

The nanoparticle solution c was irradiated with ultraviolet light. After observed by a naked eye, it was found that the solution has no or an extremely weak luminescence, and therefore it can be determined that the nanoparticle solution c was in a dispersed state.

Methanol was added to the nanoparticle solution d, and then the solution was aged for 48 hours. Subsequently, the solution was irradiated with ultraviolet light and was found to emit strong fluorescence. Therefore, it can be determined that the nanoparticle solution d was in a coagulated state.

Figure 2:
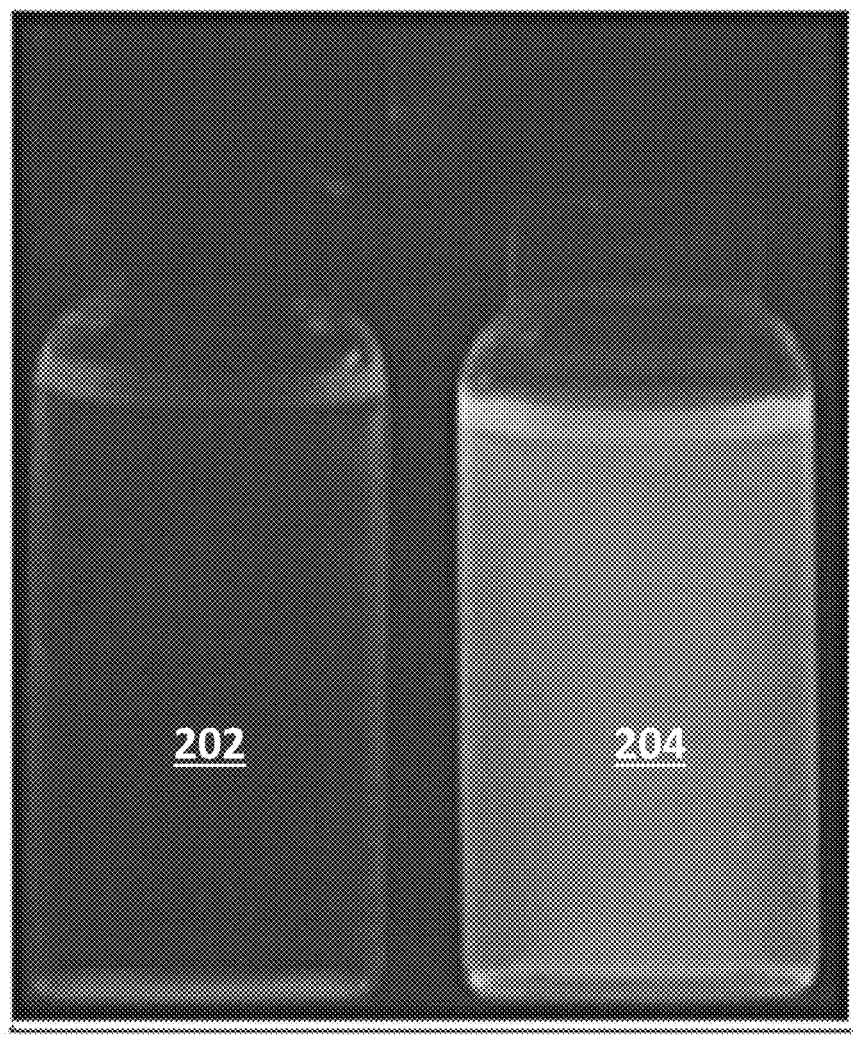
FIG. 2 is a graph comparing the luminescence of two excited solutions of the nanoparticles according to Example 2.

The luminescence state of the nanoparticle solution c and the nanoparticle solution d after irradiated by ultraviolet light was shown in FIG. 2. The left one (202) is the nanoparticle solution c and the right one (204) is the nanoparticle solution d.

Then, the nanoparticle solution c and the nanoparticle solution d were subjected to a particle size test and a luminescence intensity test respectively, and the test results were shown in Table 3 and Table 4.

TABLE 3 results of the particle size test

| nanoparticle solution c | | nanoparticle solution d | |
| --- | --- | --- | --- |
| Diameter (nm) | Volume (%) | Diameter (nm) | volume (%) |
| 3 | 5 | 3-5 | 2 |
| 4 | 18 | 6-8 | 1 |
| 5 | 40 | 209-212 | 9 |
| 6 | 22 | 213-216 | 16 |
| 7 | 15 | 219-222 | 30 |
| | | 224-226 | 18 |
| | | 227-230 | 13 |
| | | 231-234 | 4 |

It can be seen from Table 3 that the particle size of the nanoparticle solution c was below 7 nm, which indicated that the solution was obviously in a dispersed state, and the particle size of the nanoparticle solution d was up to 200 nm, which indicated that the solution was obviously in a coagulated state. Therefore, it demonstrated that the results of the dispersion detecting according to the present disclosure was consistent with the results of the particle size test.

TABLE 4 the change of the luminescence intensity and quantum yield

| | nanoparticle solution c | nanoparticle solution d | increase multiple |
| --- | --- | --- | --- |
| luminescence intensity at 620 nm | 14 | 260 | 18 |
| luminescence quantum yield | 0.01 | 0.21 | 21 |

It can be seen from Table 4 that, at 620 nm, the luminescence intensity of the nanoparticle solution d was 18 times higher than that of the nanoparticle solution c, and the luminescence yield was 21 times higher, which indicated that the luminescence of the nanoparticle solution d was much stronger than that of the nanoparticle solution c and can be observed by a naked eye.

As described above, according to the present disclosure, an aggregation-induced emission compound is modified on the surface of the nanoparticles, so that the dispersed state or aggregated and coagulated state of the nanoparticles can be indicated by the luminescence state of the compound after excited. Therefore, the dispersion detecting of the nanoparticles can be achieved by a naked eye without any complicated equipment, and the application of the coagulated nanoparticles can be avoided to save the loss.

It should be noted by those skilled in the art that the arrangements described herein are merely exemplary, and that various alternatives, modifications and improvements can be made within the scope of the disclosure. Thus, the present disclosure is not limited to the arrangements described above, but only limited by the claims.

What is claimed is:

1. A use of aggregation-induced emission compounds in dispersion detecting of nanoparticles, wherein the dispersion detecting of nanoparticles comprises:

modifying the aggregation-induced emission compounds on surfaces of the nanoparticles to obtain a modified nanoparticles solution; and exciting the modified nanoparticles solution and determining dispersion of the nanoparticles by a luminescence intensity of the modified nanoparticles solution, wherein in response to determining the luminescence intensity of the modified nanoparticles solution after being excited is lower than a first luminescence intensity, the nanoparticles are determined to be in a dispersed state; and in response to determining that the luminescence intensity of the modified nanoparticles solution after being excited is above a second luminescence intensity, the nanoparticles are determined to be in an aggregated state or a coagulated state.

2. The use according to claim 1, wherein the aggregation-induced emission compound is selected from one or more of following structures:

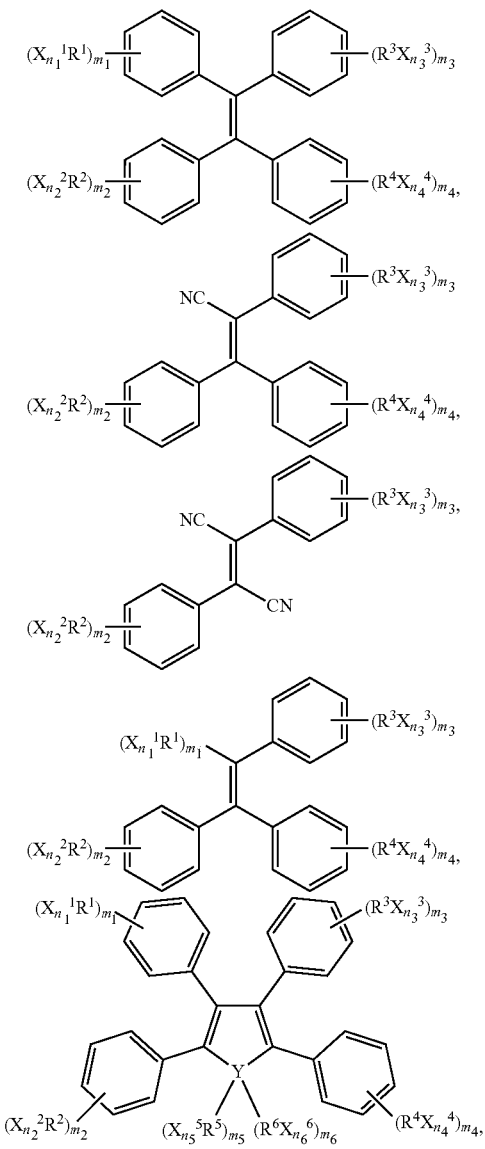

Wherein $R^1$, $R^2$, $R^3$, $R^4$, $R^5$ and $R^6$ are each independently selected from a group consisting of a chemical bond, hydrogen, a saturated alkyl group, an unsaturated alkyl group, a heteroalkyl group, a cycloalkyl group, a heterocycloalkyl group, an aryl group, a heteroaryl group and an alkoxy group;

$X^1$, $X^2$, $X^3$, $X^4$, $X^5$ and $X^6$ are each independently selected from one of an amino group, a hydroxyl group, a thiol group, a carboxyl group, a sulfonic acid group, a phosphine and a phosphine oxide;

$m_1$, $m_2$, $m_3$, $m_4$, $m_5$ and $m_6$ are each independently 1, 2 or 3;

$n_1$, $n_2$, $n_3$, $n_4$, $n_5$ and $n_6$ are each independently 0, 1, 2 or 3, and are not 0 at the same time; and Y is selected from one of C, O, N, S and Si.

3. The use according to claim 1, wherein the nanoparticles are selected from one or more of metal nanoparticles, inorganic nanoparticles, polymer nanospheres, and organic-inorganic hybrid nanoparticles.

4. The use according to claim 3, wherein the metal nanoparticles are selected from one or more of Fe, Co, Ni, Pd, Pt, Ag and Au.

5. The use according to claim 3, wherein the inorganic nanoparticles are selected from one or more of $SiO_2$, $TiO_2$, ZnO, $Si_3N_4$, CdSe and PbS.

6. The use according to claim 3, wherein the polymer nanospheres are selected from one or more of polystyrene, polylactic acid, chitosan and protein microspheres.

7. The use according to claim 1, wherein the mass ratio of the nanoparticles to the aggregation-induced emission compound is in a range from 10:1 to 1:100.

8. The use according to claim 7, wherein the mass ratio of the nanoparticles to the aggregation-induced emission compound is in a range from 3:1 to 1:3.

9. The use according to claim 1, wherein the excitation is ultraviolet light excitation, infrared light excitation, far infrared light excitation, visible light excitation or chemical energy excitation.

10. The use according to claim 1, wherein the modified nanoparticles solution after excited has a luminescence which is fluorescence, phosphorescence or delayed phosphorescence.

* * * * *